United States Patent [19]

Feldhaus et al.

[11] Patent Number: 5,759,805
[45] Date of Patent: Jun. 2, 1998

[54] CD69 TRANSCRIPTIONAL REGULATORY ELEMENTS

[75] Inventors: Andrew L. Feldhaus, Lynnwood; Steven F. Ziegler, Seattle, both of Wash.

[73] Assignee: Targeted Genetics Corporation and Immunex, Seattle, Wash.

[21] Appl. No.: 374,502

[22] PCT Filed: Jan. 20, 1995

[86] PCT No.: PCT/US95/00837

§ 371 Date: Jan. 20, 1995

§ 102(e) Date: Jan. 20, 1995

[87] PCT Pub. No.: WO95/20670

PCT Pub. Date: Aug. 3, 1995

Related U.S. Application Data

[63] Continuation of Ser. No. 188,433, Jan. 28, 1994, abandoned.
[51] Int. Cl.$^6$ .............................. C12P 21/00; C12P 19/34; C12N 15/79; C07H 21/04
[52] U.S. Cl. .................... 435/69.1; 435/91.3; 435/320.1; 435/372.3; 536/24.1
[58] Field of Search .............................. 435/69.1, 172.3, 435/240.1, 252.3, 320.1, 91.3, 372.3; 536/23.1, 23.5, 24.1

[56] References Cited

PUBLICATIONS

Hara et al., "Human T cell activation" *J. Exp. Med.* (1986) 164:1988–2005.

Cebrian et al., "Triggering of T cell proliferation through aim, an activation inducer molecule expressed on activated human lymphocytes" *J. Exp. Med.* (1988) 168:1621–1637.

Risso et al., "MLRe molecule is an activation antigen shared by human B, T lymphocytes and T cell precursors" *Eur. J. Immunol.* (1989) 19:323–328.

Cosulich et al., "Functional characterization of an antigen involved in an early step of T–cell activation" *Proc. Natl. Acad. Sci. USA* (1987) 84:4205–4209.

Lanier et al., "Interleukin 2 activation of natural killer cells rapidy induces the expression and phosphorylation of the Leu–23 activation antigen" *J. Exp. Med.* (1988) 167: 1572–1585.

Gavioli et al. "CD69 molecule in human neutrophils: Its expression and role in signal–transducing mechanisms" *Cellular Immunol.* (1992) 142:186–196.

Testi et al., "Constitutive expression of a phosphorylated activation antigen (Leu 23) by CD3$^{bright}$ human thymocytes" *J. Immunol.* (1988) 141:2557–2563.

Testi et al., "CD69 is expressed on platelets and mediates platelet activation and aggregation" *J. Exp. Med.* (1990) 172:701–707.

Nakamura et al., "Human T cell activation" *J. Exp. Med.* (1989) 169:677–689.

Testi et al., "T cell activation via Leu–23 (CD69)" *J. Immunol.* (1989) 143: 1123–1128.

Testi et al., "Leu 23 induction as an early marker of functional CD3/T cell antigen receptor triggering" *J. Immunol.* (1989) 142:1854–1860.

Moretta et al., "CD69–mediated pathway of lymphocyte activation: Anti–CD69 monoclonal antibodies trigger the cytolytic activity of different lymphoid effector cells with the exception of cytolytic T lymphocytes expressing T cell receptor α/β" *J. Exp. Med.* (1991) 174:1393–1398.

Ziegler et al., "Molecular characterization of the early activation antigen CD69: A type II membrane glycoprotein related to a family of natural killer cell activation antigens" *Eur. J. Immunol.* (1993) 23:1643–1648.

Ziegler et al., "The mouse CD69 gene" *J. Immunol.* (1994) 551:1228–1236.

Hamann et al., "Expression cloning of the early activation antigen CD69, a type II integral membrane protein with a C–type lectin domain" *J. Immunol.* (1993) 150:4920–4927.

Chambers et al., "Type II integral membrane proteins with characteristics of C–type animal lectins expressed by natural killer (NK) cells" *Glycobiology* (1993) 3:9–14.

Drickamer, "Two distinct classes of carbohydrate–recognition domains in animal lectins" *J. Biol. Chem.* (1988) 263:9557–9560.

Lenardo et al., "NF–κB: A pleiotropic mediator of inducible and tissue–specific gene control" *Cell* (1989) 58:227–229.

Staudt et al., "A lymphoid–specific protein binding to the octamer motif of immunoglobulin genes" *Nature* (1986) 323:640–643.

Klemsz et al., "The macrophage and B cell–specific transcription factor PU.1 is related to the ets oncogene" *Cell* (1990) 61:113–124.

Yamamoto et al., "Activity and tissue–specific expression of the transcription factor NF–E1 multigene family" *Genes & Development* (1990) 4:1650–1662.

Wong et al., "Ly–49 multigene family" *J. Immunol.* (1991) 147:1417–1423.

Giorda et al., "Mouse NKR–P1" *J. Immunol.* (1991) 147:1701–1708.

Bezouska et al., "Evolutionary conservation of intron position in aa subfamilly of genes encoding carbohydrate–recognition domains" *J. Biol. Chem.* (1991) 266:11604–11609.

Beavill et al., α–helical coiled–coil stalks in the low–affinity receptor for IgE (FcεRII/CD23) and related C–type lectins *Proc. Natl. Acad. Sci. USA* (1992) 89:753–757.

Lupton et al., "Dominant positive and negative selection using a hygromycin phosphotransferase–thymidine kinase fusion gene" *Mol. and Cell. Biol.* (1991) 11:3374–3378.

Allen et al., "Functional dissection of the lck proximal promoter" *Mol. and Cell. Biol.* (1992) 12:2758–2768.

(List continued on next page.)

*Primary Examiner*—Nancy Degen
*Assistant Examiner*—Robert Schwartzman
*Attorney, Agent, or Firm*—Morrison & Foerster LLP

[57] ABSTRACT

The present invention provides recombinant polynucleotides comprised of elements that regulate transcription and/or expression of coding sequences. These regulatory elements have been isolated from a CD69 gene, and thus are of particular use in regulating transcription and/or expression in cells which express CD69.

24 Claims, 18 Drawing Sheets

OTHER PUBLICATIONS

Gould et al., "Use of the DNA polymerase chain reaction for homology probing: Isolation of partial cDNA or genomic clones encoding the iron–sulfur protein of succinate dehydrogenease from several species" *Proc. Natl. Acad. Sci. USA* (1989) 86:1934–1938.

Helfman et al., "Use of antibodies of screen cDNA expression libraries prepared in plasmid vectors" *Methods in Enzymology*, (1987) ed. Berger et al., Academic Press, New York, 152:451–457.

Lewin, *Genes*, Third Edition, John Wiley & Sons, New York, pp. 213–216.

Lopez–Cabrera et la., "Molecular cloning, expression, and chromosomal localization of the human earliest lymphocyte activation antigen AIM/CD69, a new member of the C–type animal lectin superfamily of signal–transmitting receptors" *J. Exp. Med.* (1993) 178:537–547.

Sanchez–Mateos et al., "Structure–function relationship and immunochemical mapping of external and intracellular antigenic sites in the lymphocyte activation inducer molecular, AIM/CD69" *Eur. J. Immunol.* (1991) 21:2317–2325.

Matsudara, "Sequence from picomole quantities of proteins electroblotted onto polyvinylidene difluroide membranes" *J. Biol. Chem.* (1987) 262:10035–10038.

Wasylyk, "Enhancers and transcription factors in the control of gene expression" *Biochem. Biophys. Acta* (1988) 951:17–35.

Yokoyama et al., "Characterization of a cell surface–expressed disulfide–linked dimer involved in murine T cell activation" *J. Immunol.* (1988) 141:369–376.

Wasylyk (1988) Enhancers and transcription factors in the control of gene expression. Biochim. Biophys. Acta 951:17–35.

```
AGCAACTCCT GACACTTGAA AGAACTAGTC TCTGGGGAAA AAAGAAGTGA ATGCCACACG    -580

TTTTAAATCC ATAATTAACT AAATAAAACT TGTCCAATTG AGAGAGAGGG AGAGAGAGAG    -520
           →
CCACAAAGAT AGAGATTTTA AAATCCCTAC TCAACAGTAC ATCTTCTGGC CACCAACAGC    -460

ACCTGGTACA TAATGGGTAT TCAATAAATG CCTGTACCTG CCTACATATA CAAAGAAACC    -400 octamer
AATGCAAAGG ATTGCATGAA AAAGTTTTAC TCTCTCTTCC AGTGCTTTTC CATGTCAAAT    -340
```

AAG CTTTCTGTTT CCTGCACTAA    -640

Fig. 1A

```
ACAGCAATCT CCAAACTTTT AGCTCCTTGT TTAAGATTAA TACCCATTTC CTAAGTTATT   -280
                                                    NF-KB
TTGTGTTTTT AAAAAGTTTG TGGAAGGATG TCTTCGATTC TGGGAAAATC CCATTTATCT   -220
 Pu.1
CTTCCTCTTG AAGCTACAGT TGTGAGAAAG CACATTTCAG ACAGCAGGGA AAACCCGCAG   -160

CTCACCACAA CAACACACGG TGAAGTGTCT AGGCCCGCTGG AGCATAAATT AAAGAGAACT  -100
                                   Pu.1
                                                       +1
GGCTGAGTTG AGTGAGTACA GGGTAGGAGG AAGGGGGTGGA GCCTAATCGA G TATAA AGGC -40
                                                    start transcription
TGAAATCCTC CGAGATCAAG ACACTGAACA AGACAGCTCC AGCTACATCT CTCCGTGGAC    20

CACTTGAGAG TCGCCAGGGA CCTTGAGGGG AAAAAAATTA AAAGGATG                  69
```

| Fig.2A |
| Fig.2B |
| Fig.2C |
| Fig.2D |

CTGACACCCG GATGGATGGA TGATTGATG GATGGGTAGA TAGATAGATA GATAGATGGA -2020

TAGATAGATA GATAGATAGA TAGATAGATA GATAGATAGA TAGATGCACG TAAATAAATA -1960

AATATGGGGC TTGAGAGGTG ATGACTCAGT AGTACAGAGT TCTTATTGTT CTTTCAGAGG -1900

ATCAGAGTTC AGTTCCCAGC TTAAGGAAAC TCACATTGCT TGTGACTCTA ACTCCATGGA -1840

GCCTTCTTCT GTCCTCTGTG GGAACCAGCA CACACACATA TGACTCACAC ACACATAAAT -1780

ATAATGCAAT TTTTTAAAAT TAAGTTTAAT AAAGGTAAAT CAATTAAAAA ATACTCACTT -1720

Fig. 2A

```
GAGCTGCCCT TTCCTTTAA AGAGCTTAGT TAGGACCAAC ACTTATAGCA GAGGCTGGCT    -1660

ATGATGACTC TCCCTGCCTA TTTTTGTCA GTTCTGAACT CTATGAAAAC CTCATCCCAT    -1600

CCAACAGGCA TGAGTCAGAA GAGCACTTCT TGGTATTCAT GAGTATCTGG ACCTTCCTGC   -1540

TTTTCACTTG ATACTGAATT AATTACCTTA TTTATTATGG GAAAACCTGG CACATAGGCA   -1480

TATGGAAAAA GAACCGCTAA GACACAACCG AAAGACCTAA AGGCCCTGCA GTGGCAGGCT   -1420

CCTGGGCACT CCTATGGAAT AAGAAGAAGC TCTCTGTTGT AGAGGGAAAG TAATAGAGGA   -1360

AGTGCCCAGA GGCCAATGTA GAGGTTCTTC TTGGCTGTAA TGTTCTCAAC AAGATGATAT   -1300

CCTTTATTAG GAAGCCTTTG GTGAGCTGAA TGTTCTCAAC AAGATGATAT GACATACTTA   -1240

ATCTCATCCC AGCTGCTGTG CAGGAAAGAT ACTGAGAACA AAAGTCACA TTAGGACCAG    -1180

CATGTACCTG TCTGTGTCTC GAGCAGACAA ATCCACCTGC TGGCTCACCT CATTGTCTGT   -1120
```

Fig. 2B

```
GCCGNNNNNG GTACCTTCCA AGCAACCTAA GCATTATATC TTCACAAAGG GAAACCAGAC   -1060

AACTTTAGTC CAGGTCCTTT GACAATCTCT CCATTCTCTG CTCTATTCCA TATGTCAAAT   -1000

GTAGAGATCA TTCCAGAATG TAAGAAATCA TGCTTGTAAT TTTTTAAGAT CCTCACACTT   -940

GACTTACCAA AACAGACATT TTCTGCATTT ATGTGGTGCT CAATAACTTA TCTGAATGAG   -880

ATGGATATCA TGGGAAGATA TGTGTATAGG GATCATCTTC CAAATATCCG AGGCCACAGA   -820

CACCTGAAAA GGACATGGGG AAATAGAAGG AGATATTCTG CAGTGAGACA AAGTAAGTTT   -760

GACAGTGGAG GATGACAAGA AAATGAGCAA GGGATGATGA AATAGATAAC TGACGAGAAA   -700

CAGGTTTTCG ATCACACCGA GGAAGTTTCC AGACCACAAG CTTTCTGTTT CCTGCACTAA   -640

AGCAACTCCT GACACTTGAA AGAACTAGTC TCTGGGGAAA AAAGAAGTGA ATGCCACACG   -580

TTTTAAATCC ATAATTAACT AAATAAAACT TGTCCAATTG AGAGAGAGGG AGAGAGAGAG   -520
```

Fig. 2C

```
CCACAAAGAT AGAGATTTTA AAATCCCTAC TCAACAGTAC ATCTTCTGGC CACCAACAGC   -460

ACCTGGTACA TAATGGGTAT TCAATAAATG CCTGTACCTG CCTACATATA CAAAGAAACC   -400

AATGCAAAGG ATTGCATGAA AAAGTTTTAC TCTCTCTTCC AGTGCTTTTC CATGTCAAAT   -340

ACAGCAATCT CCAAACTTTT AGCTCCTTGT TTAAGATTAA TACCCATTTC CTAAGTTATT   -280

TTGTGTTTTT AAAAAGTTTG TGGAAGGATG TCTTCGATTC TGGGAAAATC CCATTTATCT   -220

CTTCCTCTTG AAGCTACAGT TGTGAGAAAG CACATTTCAG ACAGCAGGGA AAACCCGCAG   -160

CTCACCACAA CAACACACGG TGAAGTGTCT AGGCCGCTGG AGCATAAATT AAAGAGAACT   -100

GGCTGAGTTG AGTGAGTACA GGGTAGGAGG AAGGGGTGGA GCCTAATCGA GTATAAAGGC    -40

TGAAATCCTC CGAGATCAAG ACACTGAACA AGACAGCTCC AGCTACATCT CTCCGTGGAC     20

CACTTGAGAG TCGCCAGGGA CCTTGAGGGG AAAAAAATTA AAAGGATG                  69
```

Fig. 2D

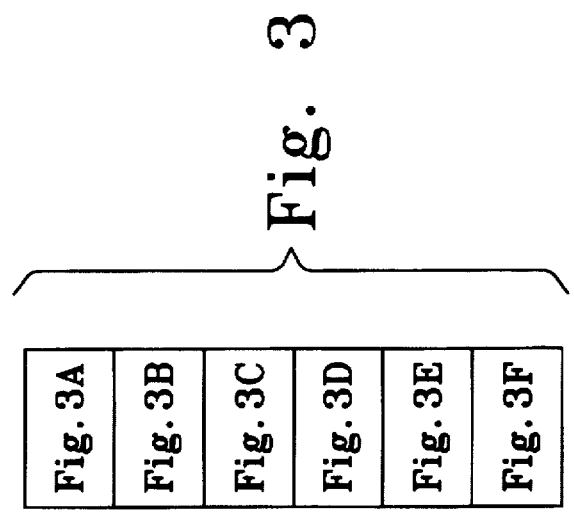

```
ATCAGAGTTC AGTCCCAGC TTAAGGAAAC TCACATTGCT TGTGACTCTA ACTCCATGGA    -1840

GCCTTCTTCT GTCCTCTGTG GGAACCAGCA CACACATACA TGACTCACAC ACACATAAAT    -1780

ATAATGCAAT TTTTAAAAT TAAGTTTAAT AAAGGTAAAT CAATTAAAAA ATACTCACTT    -1720
         #7
GAGCTGCCCT TTCCTTTAA AGAGCTTAGT TAGGACCAAC ACTTATAGCA GAGGCTGGCT    -1660

ATGATGACTC TCCCTGCCTA TTTTTGTCA GTTCTGAACT CTATGAAAAC CTCATCCCAT    -1600

CCAACAGGCA TGAGTCAGAA GAGCACTTCT TGGTATTCAT GAGTATCTGG ACCTTCCTGC    -1540

TTTTCACTTG ATACTGAATT AATTACCTTA TTTATTATGG GAAAACCTGG CACATAGGCA    -1480
```

Fig. 3B

```
TATGAAAAAA GAACCGCTAA GACACAACCG AAAGACCTAA AGCCCCTGCA GTGGCAGGCT    -1420

CCTGGGCACT CCTATGGAAT AAGAAGAAGC TCTCTGTTGT AGAGGGAAAG TAATAGAGGA    -1360 repressor  #6
 ┌─────────→
 │AGTGCCCAGA GGCCAATGTA GAGGTTCTTC TTGGCTGTAA GGTCTTTGGA TTTTAAGGAA   -1300

CCTTTATTAG GAAGCCTTTG GTGAGCTGAA TGTTCTCAAC AAGATGATAT GACATACTTA    -1240

ATCTCATCCC AGCTGCTGTG CAGGAAAGAT ACTGAGAACA AAAAGTCACA TTAGGACCAG    -1180

CATGTACCTG TCTGTGTCTC GAGCAGACAA ATCCACCTGC TGGCTCACCT CATTGTCTGT    -1120 repressor       Enh  #5
 ┌─────────→    ┌──────→
 │          │
 ↓GCCGNNNNN│G GTACCTTCCA AGCAACCTAA GCATTATATC TTCACAAAGG GAAACCAGAC  -1060
```

Fig. 3C

```
AACTTTAGTC CAGGTCCTTT GACAATCTCT CCATTCTCTG CTCTATTCCA TATGTCAAAT    -1000

GTAGAGATCA TTCCAGAATG TAAGAAATCA TGCTTGTAAT TTTTTAAGAT CCTCACACTT    -940
                                 ───────#4──────────▶

GACTTACCAA AACAGACATT TTCTGCATTT ATGTGGTGCT CAATAACTTA TCTGAATGAG    -880
──

ATGGATATCA TGGGAAGATA TGTGTATAGG GATCATCTTC CAAATATCCG AGGCCACAGA    -820

CACCTGAAAA GGACATGGGG AAATAGAAGG AGATATTCTG CAGTGAGACA AAGTAAGTTT    -760

GACAGTGGAG GATGACAAGA AAATGAGCAA GGGATGATGA AATAGATAAC TGACGAGAAA    -700

CAGGTTTTCG ATCACACCGA GGAAGTTTCC AGACCAC AAG CTT TCTGTTT CCTGCACTAA   -640
                     ◀──────#3─────── ↑Pro  Enh↲
```

Fig. 3D

```
AGCAACTCCT GACACTTGAA AGAACTAGTC TCTGGGGAAA AAAGAAGTGA ATGCCACACG   -580

TTTTAAATCC ATAATTAACT AAATAAAACT TGTCCAATTG AGAGAGAGGG AGAGAGAGAG   -520

CCACAAAGAT AGAGATTTTA AAATCCCTAC TCAACAGTAC ATCTTCTGGC CACCAACAGC   -460

ACCTGGTACA TAATGGGTAT TCAATAAATG CCTGTACCTG CCTACATATA CAAAGAAACC   -400

AATGCAAAGG ATTGCATGAA AAAGTTTTAC TCTCTCTTCC AGTGCTTTTC CATGTCAAAT   -340

ACAGCAATCT CCAAACTTTT AGCTCCTTGT TTAAGATTAA TACCCATTTC CTAAGTTATT   -280

TTGTGTTTTT AAAAGTTTTG TGGAAGGATG TCTTCGATTC TGGGAAAATC CCATTTATCT   -220
```

Fig. 3E

```
CTTCCTCCTTG AAGCTACAGT TGTGAGAAAG CACATTTCAG ACAGCAGGGA AAACCCGCAG    -160

CTCACCACAA CAACACACGG TGAAGTGTCT AGGCCGCTGG AGCATAAATT AAAGAGAACT    -100

GGCTGAGTTG AGTGAGTACA GGGTAGGAGG AAGGGGTGGA GCCTAATCGA G[TATAA]AGGC   -40
                                               → start of transcription
TGAAATCCTC CGAGATCAAG ACACTGAACA AGACAGCTCC AGCTACATCT CTCCGTGGAC     20
                                                              ← Pro
CACTTGAGAG TCGCCCAGGGA CCTTGAGGGG AAAAAAATTA AAAGGATG                 69
```

Fig. 3F

CD69 TRANSCRIPTIONAL REGULATORY ELEMENTS

CROSS-REFERENCE TO RELATED APPLICATIONS

The application is a 371 of PCT Application No. PCT/US95/00837, filed Jan. 20, 1995; which is a continuation of U.S. patent application Ser. No. 08/188,433, filed Jan. 28, 1994 (abandoned).

TECHNICAL FIELD

The production of RNA and polypeptides in recombinant systems, more specifically the use of transcription regulatory elements from the CD69 gene in the production of RNA and polypeptides.

BACKGROUND

During the process of T cell activation, the expression of several new cell-surface glycoproteins is induced. These glycoproteins are in turn involved in further aspects of cellular activation. CD69 is among the earliest of these newly synthesized cell-surface activation molecules induced on activated T cells. CD69 expression is seen within 60 minutes of T-cell stimulation, but is absent on resting cells (Hara et al., *J. Exp. Med.* 164:1988, 1986; Cosulich et al., *Proc. Acad. Sci. USA* 84:4205, 1987; and Cebrian et al., *J. Exp. Med.* 168:1621, 1988). CD69 expression is also inducible on thymocytes, B cells, natural killer (NK) cells and neutrophils (Ziegler et al., *J. Immunol.*, in press; Risso et al., *Eur. J. Immunol.* 19:323, 1989; Lanier et al., *J. Exp. Med.* 167:1572, 1988; and Gavioli et al., *Cell. Immunol.* 142:186, 1992). In addition, CD69 expression is constitutive on a subset of $CD3^{bright}$ thymocytes and platelets (Testi et al., *J. Immunol.* 141:2557, 1988; and Testi et al., *J. Exp. Med.* 172:701, 1990). While a physiological ligand for CD69 is not known, CD69 appears to be involved in cellular activation. For example, cross-linking CD69 on T cells in the presence of a second signal such as phorbol ester results in proliferation involving the induction of the interleukin-2 (IL-2) and IL-2 receptor a-chain genes (Cosulich, supra; Cebrian, supra, Nakamura et al., *J. Exp. Med.* 169:677, 1989; Risso, supra; Testi et al., *J. Immunol.* 143:1123, 1989; and Testi et al., *J. Immunol.* 142:1854, 1989). Binding of the CD69 molecule with a specific antibody is capable of activating each of the expressing cell types (Testi, 1988, supra; Testi, 1990, supra; Lanier, supra; Gavioli, supra; and Moretta et al., *J. Exp. Med.* 174:1393, 1991). CD69 expression on platelets is reported to mediate platelet activation and aggregation (Testi, 1990, supra).

Recently several groups have reported the molecular cloning of a cDNA encoding human CD69 and the mouse homolog (Ziegler et al., *Eur. J. Immuno.* 23:1643, 1993; and Hamann et al., *J. Immunol.* 150:4920, 1993). The predicted amino acid sequence of CD69 showed it to be a member of the C-type lectin family, most closely related to two families of NK cell activation molecules, NKR-P1 and Ly-49 (Chambers et al., *Glycobiology* (1993) 3:9; and Drickamer, *J. Biol. Chem.* (1988) 263:9557). These two gene families are expressed almost exclusively on NK cells and have been shown to be involved in NK cell function.

The effective use of expression vectors in recipient cells requires that the expression of the coding sequence of interest be regulated by transcriptional regulatory regions. Vectors developed for the expression of recombinant genes have utilized various viral and non-viral regulatory sequences. The ability to control the expression of recombinant genes in the appropriate cell type or in an inducible or constitutive manner is paramount for studies aimed at examining the function or therapeutic value of the recombinant gene. The invention described below presents regulatory sequences which permit both activation regulated and constitutive transcription and expression in T cells and presumably in other cell types where the CD69 gene is expressed.

SUMMARY OF THE INVENTION

The present invention provides isolated murine and human genomic DNA encoding the CD69 gene plus recombinant expression vectors containing CD69 transcription regulatory elements, including promoter, enhancer, and repressor sequences. The nucleotide sequence of the cloned CD69 promoter, enhancer, and repressor regions are provided.

Embodiments of the invention include the following.

An isolated polynucleotide consisting essentially of a CD69 promoter or active fragment thereof.

A recombinant polynucleotide comprised of a CD69 promoter or active fragment thereof.

An isolated polynucleotide consisting essentially of a CD69 enhancer or active fragment thereof.

A recombinant polynucleotide comprised of a promoter operably linked to a CD69 enhancer or active fragment thereof.

A recombinant expression vector comprised of a polynucleotide coding sequence encoding a polypeptide operably linked to a promoter and CD69 promoter enhancer.

An isolated CD69 gene, selected from the group consisting of mouse and human CD69 genes.

An isolated polynucleotide consisting essentially of a CD69 repressor or active fragment thereof.

A recombinant polynucleotide comprised of a promoter operably linked to a CD69 repressor or active fragment thereof.

A recombinant expression vector comprised of a polynucleotide coding sequence encoding a polypeptide operably linked to a promoter and CD69 repressor.

A recombinant host cell comprised of a polynucleotides, including expression vectors, described above.

A method of producing a desired RNA comprising incubating a host cell transformed with a recombinant polynucleotide comprised of a CD69 promoter or active fragment thereof operably linked to a segment encoding the desired RNA, wherein the incubation is under conditions that allow transcription.

A method of producing a desired RNA comprising incubating a host cell transformed with a recombinant polynucleotide comprised of a CD69 enhancer or active fragment thereof operably linked to a segment encoding the desired RNA and a promoter, wherein the incubation is under conditions that allow transcription.

A method of producing a desired RNA comprising incubating a host cell transformed with a recombinant polynucleotide comprised of a CD69 repressor or active fragment thereof operably linked to a segment encoding the desired RNA and a promoter, wherein the incubation is under conditions that allow transcription.

A method of producing a polypeptide comprising incubating a host cell transformed with a recombinant polynucleotide encoding a polypeptide, including expression vectors, as described above.

BRIEF DESCRIPTION OF THE DRAWINGS

FIG. 1 (positions 1418 through 2149 of SEQ ID NO:1) presents the sequence of a polynucleotide of 732 base pairs of nucleotides including the ATG initiation codon of the mouse CD69 gene.

FIG. 2 (SEQ ID NO:1) presents the sequence of a polynucleotide that contains the CD69 repressor, CD69 enhancer, and CD69 promoter elements.

FIG. 3 (SEQ ID NO:1) presents the sequence of the polynucleotide of FIG. 2 indicating the placement of the promotor, enhancer, and repressor elements.

DETAILED DESCRIPTION OF THE INVENTION

Figure 4:
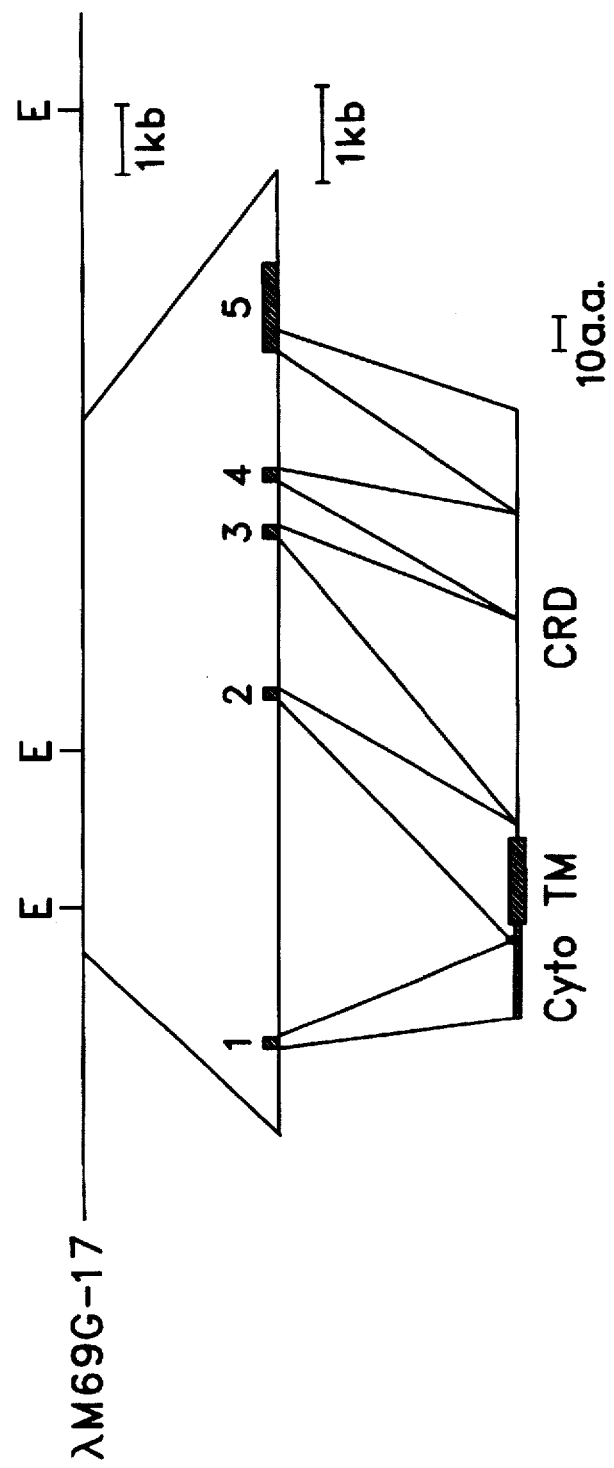
FIG. 4 is a diagram of the structure of a mouse CD69 gene, including the intron and exon and 5'-upstream sequence placements.

The initiation stage of messenger RNA synthesis is a major site for regulation of gene expression. In eukaryotes, initiation is governed by DNA sequence elements comprising several functional classes. These include a core promoter element, which contains the binding site for RNA polymerase II and controls the location of the site of transcription initiation, and upstream promoter elements and enhancers, which regulate the rate at which RNA polymerase II initiates new rounds of transcription from the core promoter. These sequence elements direct the action of two classes of transcription factors: general initiation factors, which are essential for initiation and which are sufficient to direct a basal level of transcription from many core promoters, and regulatory factors which are not required for initiation but which mediate the action of upstream promoter elements and enhancers.

The present invention provides transcriptional regulatory elements isolated from CD69 genes, including promoters, enhancers, and repressors. These transcriptional regulatory elements are of use in controlling the transcription of polynucleotide sequences to which they are operably linked, and thus they may also lend a level of control to the expression of genes from recombinant molecules. In addition, the present invention provides clones containing the genomic sequences of human and mouse CD69.

The practice of the present invention will employ, unless otherwise indicated, conventional techniques of molecular biology, microbiology, recombinant DNA, and immunology, which are within the skill of the art. Such techniques are explained fully in the literature. See e.g., Sambrook, Fritsch, and Maniatis, MOLECULAR CLONING: A LABORATORY MANUAL, Second Edition (1989), OLIGONUCLEOTIDE SYNTHESIS (M. J. Gait Ed., 1984), ANIMAL CELL CULTURE (R. I. Freshney, Ed., 1987), the series METHODS IN ENZYMOLOGY (Academic Press, Inc.); GENE TRANSFER VECTORS FOR MAMMALIAN CELLS (J. M. Miller and M. P. Calos eds. 1987), HANDBOOK OF EXPERIMENTAL IMMUNOLOGY, (D. M. Weir and C. C. Blackwell, Eds.), CURRENT PROTOCOLS IN MOLECULAR BIOLOGY (F. M. Ausubel, R. Brent, R. E. Kingston, D. D. Moore, J. G. Siedman, J. A. Smith, and K. Struhl, eds., 1987), and CURRENT PROTOCOLS IN IMMUNOLOGY (J. E. Coligan, A. M. Kruisbeek, D. H. Margulies, E. M. Shevach and W. Strober, eds., 1991). All patents, patent applications, and publications mentioned herein, both supra and infra, are incorporated herein by reference.

As used herein, the "CD69" promoter is a polynucleotide derived from a CD69 gene that contains at least the "core promoter" element, i.e., that element necessary to initiate transcription by RNA polymerase II. The TATA box, usually located 25 to 30 base pairs (bp) upstream of the transcription initiation site, is thought to be involved in directing RNA polymerase II to begin RNA synthesis at the correct site. In addition, the CD69 promoter may contain additional elements that control transcription of an operably linked downstream sequence by binding one or more general initiation factors. These elements can act regardless of their orientation, but they are usually located within 100 to 200 bp upstream of the TATA box. The upstream promoter elements usually affect the rate at which transcription is initiated.

An "active fragment" of a promoter is that portion of the promoter which is essential for directing RNA polymerase II to begin RNA synthesis at the correct site in T cells or other cells in which CD69 is usually expressed. Thus, an "active fragment" of a CD69 promoter encompasses the TATA box and has a minimum of about 200 nucleotides of the contiguous sequence of a CD69 promoter, preferably at least about 400 nucleotides of the contiguous sequence of a CD69 promoter, and may even have at least about 600 nucleotides of the contiguous sequence of a CD69 promoter.

An example of a CD69 promoter is shown in FIG. 1. The Figure presents the sequence of a polynucleotide of 732 base pairs of nucleotides including the ATG initiation codon of the mouse CD69 gene. The nucleotides upstream of the ATG start codon are indicated by negative numbers. A polynucleotide comprised of the promoter was isolated by polymerase chain reaction (PCR) amplification of a region that is 5'-upstream of the coding sequences of the mouse CD69 gene. Promoter activity was tested in transient transfection and stable transfection systems in a T cell line, using a segment of the chloramphenicol acyltransferase gene containing the coding sequence as a reporter gene.

An inspection of the sequence of the isolated polynucleotide comprised of the CD69 promoter reveals a canonical TATA box sequence (indicated by the boxed sequence) but not a CCAAT site. Also present are several potential binding sites for known transcription factors, including NFkB (Lenardo, et al., *Cell* (1989) 58:227), Oct-1/Oct-2 (Staudt, et al., *Nature* (1986) 323:640), PU.1 (Klemsz, et al., *Cell* (1990) 61:113), and the GATA family (Yamamoto, et al., *Genes Dev.* (1990) 4:1640). The functionality of the polynucleotide comprised of this CD69 promoter in promoting transcription is shown in the Examples. Generally, methods of detecting promoter functionality are known in the art (see, for example, Sambrook, et al.*Molecular Cloning: A Laboratory Manual*, Cold Spring Harbor Press, Cold Spring Harbor, N.Y.), and include, for example, the measurement of transcription of mRNA or the expression of a polypeptide from a reporter gene which requires the addition of a functional promoter.

A CD69 promoter in a recombinant polynucleotide is expected to be functional in eukaryotic cells, particularly in cells in which CD69 is usually expressed, including activated thymocytes and T cells. In both transient and stably transfected Jurkat cells, the promoter exhibited relatively low levels of activity in the absence of an enhancer element, but was stimulated by either the CMV or CD69 the enhancer. Surprisingly, it was found that the CD69 promoter in a recombinant polynucleotide responded differently in transient transfection systems and in stable transfection systems with respect to an inducer, for example phorbol myristic acid in combination with ionomycin (PI).

As used herein, the term "operably linked" refers to a juxtaposition wherein the components so described are in a relationship permitting them to function in their intended manner. A control sequence "operably linked" to another control sequence and/or to a coding sequence is ligated in such a way that transcription and/or expression of the coding sequence is achieved under conditions compatible with the control sequence.

A "coding sequence" is a polynucleotide sequence which is transcribed into RNA, usually mRNA, and/or translated into a polypeptide when placed under the control of appropriate regulatory sequences.

The term "polynucleotide" as used herein refers to a polymeric form of nucleotides of any length, either ribonucleotides or deoxyribonucleotides. This term refers only to the primary structure of the molecule. Thus, this term includes double- and single-stranded DNA and RNA. It also includes known types of modifications, for example, labels which are known in the art (e.g., Sambrook, et al.), methylation, "caps", substitution of one or more of the naturally occurring nucleotides with an analog, internucleotide modifications such as, for example, those with uncharged linkages (e.g., methyl phosphonates, phosphotriesters, phosphoamidates, carbamates, etc.), those containing pendant moieties, such as, for example, proteins (including for e.g., nucleases, toxins, antibodies, signal peptides, poly-L-lysine, etc.), those with intercalators (e.g., acridine, psoralen, etc.), those containing chelators (e.g., metals, radioactive metals, boron, oxidative metals, etc.), those containing alkylators, those with modified linkages (e.g., alpha anomeric nucleic acids, etc.), as well as unmodified forms of the polynucleotide.

The invention includes as an embodiment an isolated polynucleotide comprised of a CD69 promoter or active fragment thereof. These isolated polynucleotides contain less than about 50%, preferably less than about 70%, and more preferably less than about 90% of the chromosomal genetic material with which the CD69 promoter is usually associated in nature. An isolated polynucleotide "consisting essentially of" a CD69 promoter lacks other promoters derived from the chromosome on which CD69 is located. This terminology of "isolated" and "consisting essentially of" is analagously applicable to CD69 enhancer and CD69 repressor elements. For example, an isolated polynucleotide consisting essentially of a CD69 enhancer or repressor lacks other enhancers or promoters, respectively, located on the chromosome on which CD69 is located.

Isolated polynucleotides comprised of or consisting essentially of a CD69 promoter, CD69 enhancer, CD69 repressor or active fragments thereof, may be prepared by techniques known in the art (e.g., Sambrook, et al.). These techniques include, for example, using the sequence information provided herein to provide primers and probes to amplify by PCR specific regions of CD69 genomic clones, or by chemical synthesis, or by recombinant means. In addition, for example, the deposited clones including the murine CD69 genomic sequences, can be grown in $E.\ coli$ and the plasmids purified by standard plasmid DNA preparation techniques. The murine promoter can be isolated from the remainder of the plasmid by a HindIII-BamHI restriction enzyme digest. The murine CD69 enhancer can be purified from the remainder of the plasmid by a HindIII restriction enzyme digestion. Similarly, the deposited clones containing the human genomic CD69 sequences may be used to isolate the human transcriptional control elements upstream of the ATG start codon using appropriate restriction enzymes.

The term "recombinant polynucleotide" as used herein intends a polynucleotide of genomic, cDNA, semisynthetic, or synthetic origin which, by virtue of its origin or manipulation: (1) is not associated with all or a portion of a polynucleotide with which it is associated in nature; or (2) is linked to a polynucleotide other than that to which it is linked in nature; or (3) does not occur in nature.

A recombinant polynucleotide comprised of a CD69 promoter or active fragment thereof, as well as those which may be comprised of other CD69 transcriptional regulatory elements described herein, may be prepared by any technique to those of skill in the art using the sequence information provided herein.

A recombinant polynucleotide comprised of a CD69 promoter may also be comprised of a coding sequence to which the promoter is operably linked, causing transcription of the coding sequence under the control of the promoter. Coding sequences may encode either homologous or heterologous polypeptides. However, they may also encode other moieties which are desirable in their transcribed form. For example, coding sequences may encode, inter alia, decoy polynucleotides that bind to transcription factors, anti-sense RNAs, and a variety of polypeptides that are of interest (e.g. viral proteins to serve as intracellular vaccines, proteins that serve as markers, etc.), polypeptides for commercial purposes that are to be expressed in cells that express CD69proteins, and particularly proteins that are of use in gene therapy.

The term "polypeptide" refers to a polymer of amino acids and does not refer to a specific length of the product; thus, peptides, oligopeptides, and proteins are included within the definition of polypeptide. This term also does not refer to or exclude post-expression modifications of the polypeptide, for example, glycosylations, acetylations, phosphorylations and the like. Included within the definition are, for example, polypeptides containing one or more analogs of an amino acid (including, for example, unnatural amino acids, etc.), polypeptides with substituted-linkages, as well as the modifications known in the art, both naturally occurring and non-naturally occurring.

The CD69 regulatory sequences described herein can be used to control the transcription and/or expression of linked coding sequences. Potential uses include the generation of expression libraries in cells where the CD69 sequences are active (e.g. T cells, B cells, macrophages, etc.) and the generation of expression vectors for use in vitro or in vivo in transgenic mice, to name a few.

The polynucleotide comprised of a CD69 regulatory sequence, including those containing a CD69 promoter and coding sequence may also contain those elements which allow its replication and/or selection within a host cell. These elements include, for example, an origin of replication and a selection gene.

Also contemplated within the invention are expression vectors comprised of a CD69 promoter operably linked to a coding sequence. Expression vectors generally are replicable polynucleotide constructs that encode a polypeptide operably linked to suitable transcriptional and translational regulatory elements. Examples of regulatory elements usually included in expression vectors are promoters, enhancers, ribosomal binding sites, and transcription and translation initiation and termination sequences. The regulatory elements employed in the expression vectors containing the CD69 promoter would be functional in the host cell used for expression.

The invention also provides a polynucleotide comprised of a CD69 enhancer element. As used herein, the term "enhancer" refers to an element of a polynucleotide that stimulates transcription from a linked homologous or heterologous promoter. An enhancer often exhibits stimulatory activity when placed in either orientation, and certain enhancers may be active when placed downstream from the transcription initiation site or at considerable distances from the promoter. Methods for detecting enhancer activity are known in the art, for e.g., see Molecular Cloning, A Laboratory Manual, Second Edition, (Sambrook Fritsch, Maniatis, Eds., Cold Spring Harbor Laboratory Press, Cold Spring Harbor N.Y., 1989).

A polynucleotide comprised of a CD69 enhancer element was isolated from a region 5' to the coding sequence of the mouse CD69 gene. The sequence of this polynucleotide is illustrated in FIG. 2 as nucleotides −1131 to +67. A fragment of the polynucleotide in FIG. 2 that exhibited enhancer activity is shown in FIG. 3, wherein the symbols of upstream and downstream arrows and "Enh" indicate the fragment with activity. The activity of the CD69 enhancer element in the polynucleotide was examined in a white blood cell line, Jurkat cells. Enhancer activity was demonstrated using the CD69 promoter, an IL-2Rα promoter and a-minimal thymidine kinase (TK) promoter. Moreover enhancer activity was demonstrated when the enhancer was in either the 3'- or 5'-orientation relative to the promoter and coding sequence.

The CD69 enhancer element surprisingly appears to be as strong an enhancer as that derived from cytalomegalovirus (CMV), may be used with homologous and heterologous promoters, and provides a product that is of non-viral origin. Thus, included within the invention is a polynucleotide comprised of a CD69 enhancer element that may be used to enhance transcription of coding sequences under a variety of circumstances.

In some embodiments of the invention a CD69 enhancer will be present in a recombinant polynucleotide comprised of a promoter to which the enhancer is operably linked; these recombinant polynucleotides include expression vectors as described above. The promoter to which the enhancer is operably linked may be homologous or heterologous to the enhancer.

Another embodiment of the invention is an isolated polynucleotide containing a repressor element discovered within the CD69 gene. A polynucleotide fragment containing a CD69 repressor element is shown in FIG. 3. The fragment is indicated as #6 and is flanked by two arrows. A "repressor element" as used herein down-regulates transcription from an operably linked promoter and/or promoter-enhancer complex; this down-regulation may be all or partially reversed by the presence of an inducer substance.

The CD69 repressor element may be included in a recombinant polynucleotide when it is desirable to control the transcription and/or expression of an operably linked coding sequence by the presence or absence of an inducer that interacts via the repressor. Thus, embodiments of the invention include recombinant polynucleotides and recombinant expression vectors comprised of a CD69 repressor. These recombinant polynucleotides may contain a CD69 repressor, an enhancer, preferably a CD69 enhancer, a CD69 promoter, and a coding sequence to which these regulatory elements are operably linked.

The invention also includes recombinant host cells comprised of any of the above described polynucleotides that contain a CD69 promoter and/or CD69 enhancer and/or CD69 repressor. The polynucleotides may be inserted into the host cell by any means known in the art. As used herein, "recombinant host cells", "host cells", "cells", "cell lines", "cell cultures", and other such terms denoting microorganisms or higher eukaryotic cell lines cultured as unicellular entities refer to cells which can be, or have been, used as recipients for recombinant vector or other transfer DNA, and include the progeny of the original cell which has been transformed. It is understood that the progeny of a single parental cell may not necessarily be completely identical in morphology or in genomic or total DNA complement as the original parent, due to natural, accidental, or deliberate mutation.

"Transformation", as used herein, refers to the insertion of an exogenous polynucleotide into a host cell, irrespective of the method used for the insertion, for example, direct uptake, transduction, f-mating or electroporation. The exogenous polynucleotide may be maintained as a non-integrated vector, for example, a plasmid, or alternatively, may be integrated into the host cell genome.

Also included within the invention are antisense polynucleotides and decoys to the promoter, enhancer, and repressor elements of the CD69 gene. These polynucleotides may be prepared by a variety of techniques known in the art, including chemical synthesis and recombinant technology. Antisense polynucleotides to the transcription elements may be used in the regulation of transcription of a polynucleotide sequence to which the regulatory element is operably linked, including the polypeptide encoded by the CD69 gene.

The following listed materials are on deposit under the terms of the Budapest Treaty with the American Type Culture Collection (ATCC), 12301 Parklawn Dr., Rockville, Md. 20852, and have been assigned the following Accession Numbers.

Murine CD69 promotor in BLCAT2 vector number 75653 deposited on Jan. 25, 1994; Murine CD69 enhancer in BLCAT2 vector number 75654 deposited on Jan. 25, 1994; Murine CD69 repressor in BLCAT2 vector #75660, deposited on Jan. 27, 1994; Murine CD69 genomic clone in pBluescript KS contains the promotor and sequence through Exon 1 vector #69541, deposited on Jan. 27, 1994; Murine CD69 genomic clone in pBluescript KS contains the sequence from the end of Exon 1 through Exon 4 vector #69539, deposited on Jan. 25, 1994; Murine CD69 genomic clone in pBluescript KS contains the sequence from the end of Exon 4 through Exon 5 vector #69538, deposited on Jan. 25, 1994; Human CD69 genomic clone in Supercos vector contains entire gene vector #69540, deposited on Jan. 25, 1994. Upon allowance and issuance of this application as a United States Patent, all restriction on availability of these deposits will be irrevocably removed; and access to the designated deposits will be available during pendency of the above-named application to one determined by the Commissioner to be entitled thereto under 37 C.F.R. §1.14 and 35 U.S.C. §122. Moreover, the designated deposits will be maintained for a period of thirty (30) years from the date of deposit, or for five (5) years after the last request for the deposit; or for the enforceable life of the U.S. patent, whichever is longer. The deposited materials mentioned herein are intended for convenience only, and are not required to practice the present invention in view of the descriptions herein, and in addition these materials are incorporated herein by reference.

The following examples are provided only for illustrative purposes, and not to limit the scope of the present invention. In light of the present disclosure numerous embodiments within the scope of the claims will be apparent to those of ordinary skill in the art.

EXAMPLES

Example 1

Isolation of the Murine CD69 Gene

A C57BL/6 genomic library in λFix II (Stratagene) was screened with a mouse CD69 cDNA probe. (The illustrative vectors used in the Examples are widely available; see, e.g., the Stratagene catalog, which describes the pBluescript® SK±phagemids (Stratagene catalog #212201 (SK+) and 212202 (SK−), GenBank #52325 (SK+) and 52324 (SK−)); the Lambda Fix® II vector for genomic cloning (Stratagene catalog #248201); the SuperCos 1 cosmid vector (Stratagene catalog #251301); and the pWE15 cosmid vector (Stratagene catalog #251201); see also the chimeric CAT fusion genes described by B. Luckow et al. (1987) Nucl. Acids Res. 15:5490 and following. Many other suitable vectors are also known in the art and are generally available). Several clones were isolated and analyzed by hybridization to a series of oligonucleotide probes that spanned the sequence of the mouse CD69 cDNA. One clone, λM69G-17, contained the entire CD69 coding region. A 2.4 Kb HindIII fragment which included the 5' terminus of the cDNA and two overlapping regions which contained additional 5' CD69 sequences were subcloned into pBluescript KS (Stratagene). A 5.0 Kb KpnI-EcoRI clone was subcloned into pBluescript KS. The resulting clone contains additional 5' CD69 sequences.

Example 2

Structure of the CD69 gene

To assess copy number and any possible polymorphisms in the CD69 gene, DNA isolated from a variety of mouse strains was digested with either XbaI or EcoRI, transferred to filters and hybridized with a mouse CD69 cDNA probe. The CD69 probe hybridized to two fragments generated by a given enzyme from DNA of all strains tested. These data strongly suggest that the CD69 gene is a single-copy gene and not polymorphic.

To further analyze the mouse CD69 gene, a phage library made from C57BL/6 genomic DNA was screened with a murine CD69 cDNA probe. Several clones were isolated and one clone, λM69G-17, hybridized with oligonucleotide probes that spanned the mouse CD69 cDNA. This clone was further mapped and the exon/intron borders were determined by direct nucleotide sequencing. FIG. 4 shows the structure of the mouse CD69 gene as determined from clone λM69G-17. The gene spans approximately 7.5 kB of DNA and contains 5 exons. The intron sequence at each exon/intron junction conforms to the canonical GT . . . AG (Table I).

TABLE I

Exon/Intron Sequences of the Mouse CD69 Gene[a]

| | Q | $K_{21}$ | intron | $D_{22}H$ | G | |
|---|---|---|---|---|---|---|
| Exon 1 . . . | CAG | AAG | G/gt . . . ag/ | AC CAT | GGC | . . . Exon 2 |

| | | L | $N_{62}$ | | $V_{63}G$ | K | |
|---|---|---|---|---|---|---|---|
| Exon 2 . . . | TTA | AAT | G/gt . . . ag/ | TG | GGC | AAG | . . . Exon 3 |

| | | Q | $M_{129}$ | | $T_{130}$ | F | |
|---|---|---|---|---|---|---|---|
| Exon 3 . . . G | GAC | ATG/gt . . . ag/ | ACG | TTT | C | . . . Exon 4 |

| | N | S | $W_{164}$ | | $F_{165}$ | F | |
|---|---|---|---|---|---|---|---|
| Exon 4 . . . AC | AGC | TG/gt . . . ag/ | G | TTC | AAC | . . . Exon 5 |

[a]Sequences at the exon/intron junctions in the mouse CD6 gene. Exonic sequences are upper case and intronic sequences are lower case. The amino acids at the junctions are numbered as in Ziegler et al. Em. J. Immunol. (1993) 23 1643.

Exon 1 encodes the cytoplasmic domain, exon 2 the membrane-spanning domain, and exons 3–5 encode the carbohydrate recognition domain (CRD). There is conservation in the placement of introns in the CRD between the genes for NKR-P1, Ly-49, as well as CD23, the asialoglycoprotein receptor, and the mouse CD69 gene (data not shown and Wong et al. J. Immunol. (1991) 147: 1417; Giorda, et al., J. Immunol. (1991) 147:1701; Bezouska, et al., J. Biol. Chem. (1991) 266:11604). However, while CD69 is encoded by 5 exons, these other proteins are encoded by at least 6 exons (Bezouska, et al.). The protein sequence contained in these other C-type lectins that is lacking in CD69 is predicted to lie between the plasma membrane and the CRD. This has been proposed to form an α-helical coiled-coil that is believed to serve as a stalk for the CRD (Beavil, et al., Proc. Natl. Acad. Sci. USA (1992) 89:753).

Example 3

CD69 Promoter Analysis By Transient Transfection

A DNA fragment comprising the 5' untranslated region of the murine cDNA and 662 base pairs of 5' upstream genomic DNA sequences was amplified by the PCR procedure. The DNA template for PCR was the 2.4H clone in pBluescript ks (Stratagene) of Example 1. The 5' primer employed in the PCR reaction was a single-stranded oligonucleotide comprising a sequence identical to the T3 primer (Stratagene). The 3' primer was a single-stranded oligonucleotide comprising a sequence complementary to the murine CD69 cDNA sequence from position +67 to +38 (position +1 being the 5' end of the murine cDNA). The 3' primer additionally comprises an EcoRI site go that the amplified fragment will contain an EcoRI restriction site downstream of the CD69 sequences.

PCR was conducted according to conventional procedures. The following PCR reagents were added to a 0.5 mL Eppendorf tube: 10 μl of 10 X PCR buffer (500 mM KCl, 100 mM Tris-HCl, pH 8.3, 25 mM $MgCl_2$, and 1 mg/mL gelatin), 10 μl of a 2.0 mM solution containing each dNTP (2 mM dATP, 2 mM dGTP, 2 mM dCTP, and 2 mM dTTP), 2 ng template, 100 pg of each oligonucleotide primer, 2.5 units of Taq DNA polymerase (Perkins-Elmer Cetus), and $H_2O$ to a final volume of 100 μl. PCR was carried out using a Gene Amp PCR System 9600 (Perkins-Elmer Cetus). The template was denatured at 94° C. for 5 minutes and PCR was carried out for 30 cycles of amplification using a step program (denaturation at 94° C., 1 minute; annealing at 54° C., 1 minute; extension at 72° C., 1 minute).

The amplified DNA was resolved and recovered from a low-gelling temperature agarose gel and digested with EcoRI and HindIII (the latter site is present in the CD69 sequence at position –662). The fragment was repurified on a low-gelling-temperature agarose gel and inserted into the EcoRI and HindIII sites of pBluescript (Stratagene) and named pSKCD69 HB. The CD69 sequences were transferred to HyTK lck-7 CAT as a HindIII-BamHI fragment (BamHI site is present in the polylinker region of pBluescript) and named HyTK-CD69HB-CAT. HyTK-CD69HB-CAT and HyTK lck-7CAT are derived from the HyTK vector described in Lupton et al., Mol. Cell Biol. 11:3374 (1991). HyTK lck-7CAT contains the CAT reporter gene under the control of the lck promotor sequences (–37 to –72) (Allen, et al., Mol. Cell Biol. (1992) 12:2758. HyTK-CMV-CAT was a similar construct to HyTK-CD69HB-CAT, except that the CMV promoter/enhancer complex replaced the CD69 promoter. The CMV promotor and enhancer was PCR amplified. Primers contained a 5' HindIII and a 3' BamHI restriction site. The PCR product was cloned into the HindIII-BamHI sites of the HyTK lck-7CAT replacing the lck sequences.

Figure 5:
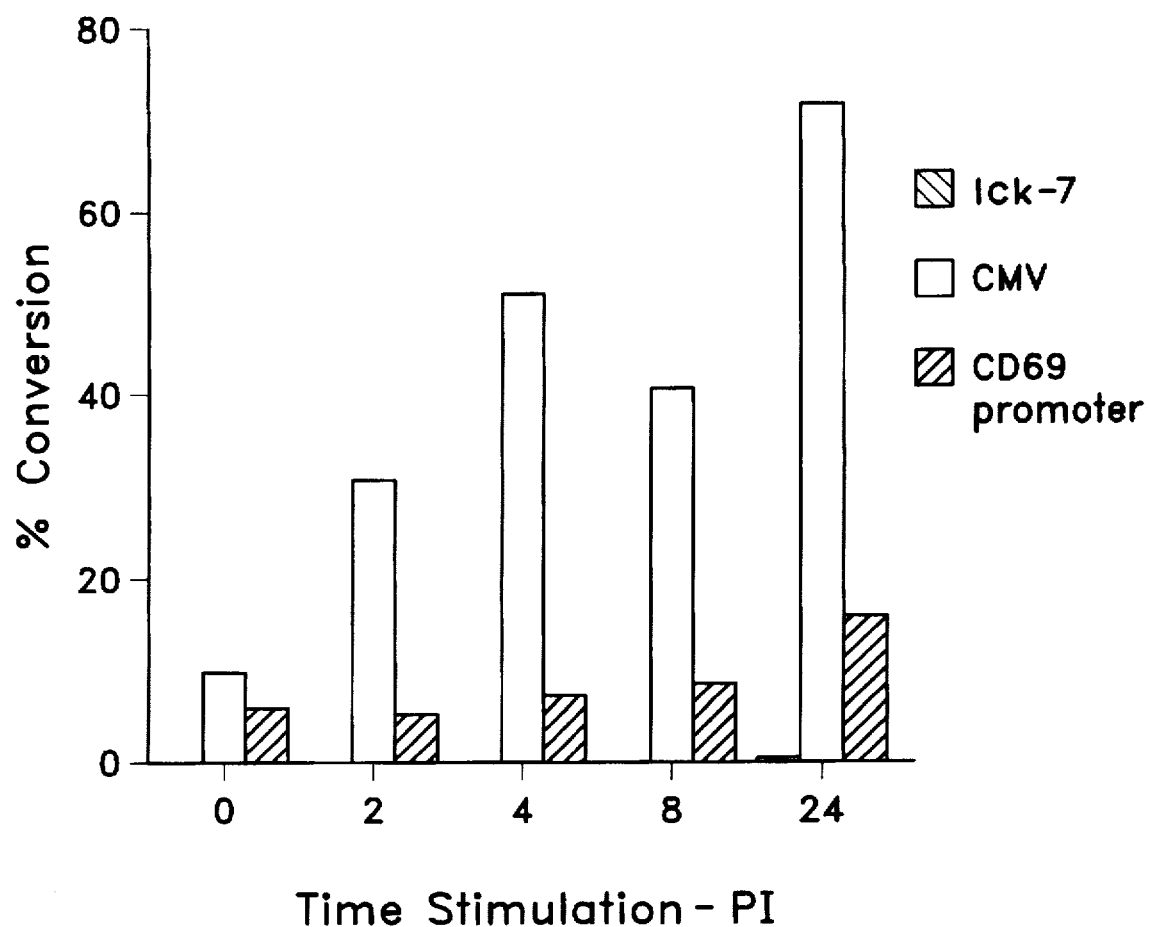
FIG. 5 is a bar graph illustrating CD69 promoter activity as compared to CMV promoter/enhancer activity in transient transfections of Jurkat cells; the activities are indicated as chloramphenicol acetyltransferase activity before and after stimulation with phorbol myristic acid and ionomycin (PI).

The ability of the CD69 sequences to promote transcription of the chloramphenicol acetyl transferase (CAT) reporter gene was tested by transient transfection of the HyTK-CD69HB-CAT construct into Jurkat cells. Jurkat cells are a CD4+-transformed cell line. Expression of CD69 in these cells is absent unless stimulated with any of a variety of agents capable of activating T cells. The transient transfections contained positive and negative CAT constructs. HyTK-CMV-CAT has the CAT reporter gene under the very active CMV promoter/enhancer sequences, and HyTK-lck-7-CAT is a promoterless construct which is not active in Jurkat cells. Fifty micrograms of HyTK-CD69HB-CAT and HyTK-lck-7-CAT and 10 µg of HyTK-CMV-CAT were electroporated into Jurkat cells as follows. Jurkat cells at a density of $5 \times 10^5$ cells/mL were pelleted and resuspended in complete RPMI 1640 medium (10% fetal bovine serum, 0.1 mM nonessential amino acids, 50 µM 2-mercaptoethanol, 2 mM L-glutamine, 50 U/mL penicillin, and 50 µg/mL streptomycin) at a density of $4 \times 10^6$ cells/800 µl. DNA and 800 µl of cells were mixed and electroporated at 300 volts and 960 µF using a Bio-Rad Gene Pulser. All transfections were done in duplicate. The cells were then transferred to 10 mL complete medium and incubated in a 37° C., 5% $CO_2$ incubator for 12–15 hours. After the incubation period one set of the duplicate transfections were stimulated with PMA (10 ng/mL) and ionomycin (500 ng/mL) for 24 hours. Cells were subsequently harvested by centrifugation, resuspended in 0.25M Tris, pH 8.0 and subjected to three cycles of freeze/thaw to lyse the cells. Standard CAT reaction assays followed by thin-layer chromatography were utilized to determine CAT activity (Sambrook et al. in Molecular Cloning: A Laboratory Manual). Quantitation of the CAT assays was performed on the Phosphorimager SF (Molecular Dynamics). The results of the study are shown in FIG. 5. The CD69 sequences displayed very weak promoter activity which was not induced by the PMA/ionomycin (PI) stimulation.

Addition of the CMV enhancer 5' of the CD69HB promoter sequences resulted in a construct named HyTK-CMV-CD69HBG-CAT. The CMV enhancer was amplified by PCR from the HyTK-CMV CAT construct. Both primers contained a HindIII clone site. The CMV enhancer was then cloned into the HindIII site of the HyTK-CD69HB-CAT. The HindIII site is immediately 5' of the CD69 sequences. Transient transfection of this construct into Jurkat cells resulted in high CAT activity in both stimulated and unstimulated cells. The CD69 sequences serve as a promoter in Jurkat cells but its activity is not regulated by the stimulated state of the cells when assayed by transient transfections.

Example 4

CD69 Promoter Analysis by Stable Transfection

The HyTK-CD69HB-CAT, HyTK-CMV-CAT, and HyTK-lck-7-CAT constructs were stably transfected into Jurkat cells as follows. Transfections were performed as described for transient transfections in Example 3 except that 10 µg of DNA was transfected. Twenty-four hours post-transfection the Jurkat cells were placed under selection by the addition of 350 µg/mL of hygromycin B. Cells were cultured in the presence of drug selection for 3–4 weeks at which time polyclonal populations had emerged. A total of $2 \times 10^6$ cells in 10 mL medium were incubated for 24 hours either in the presence or absence of PI (see Example 3) and subsequently analyzed-for CAT activity as described in Example 3.

Figure 6:
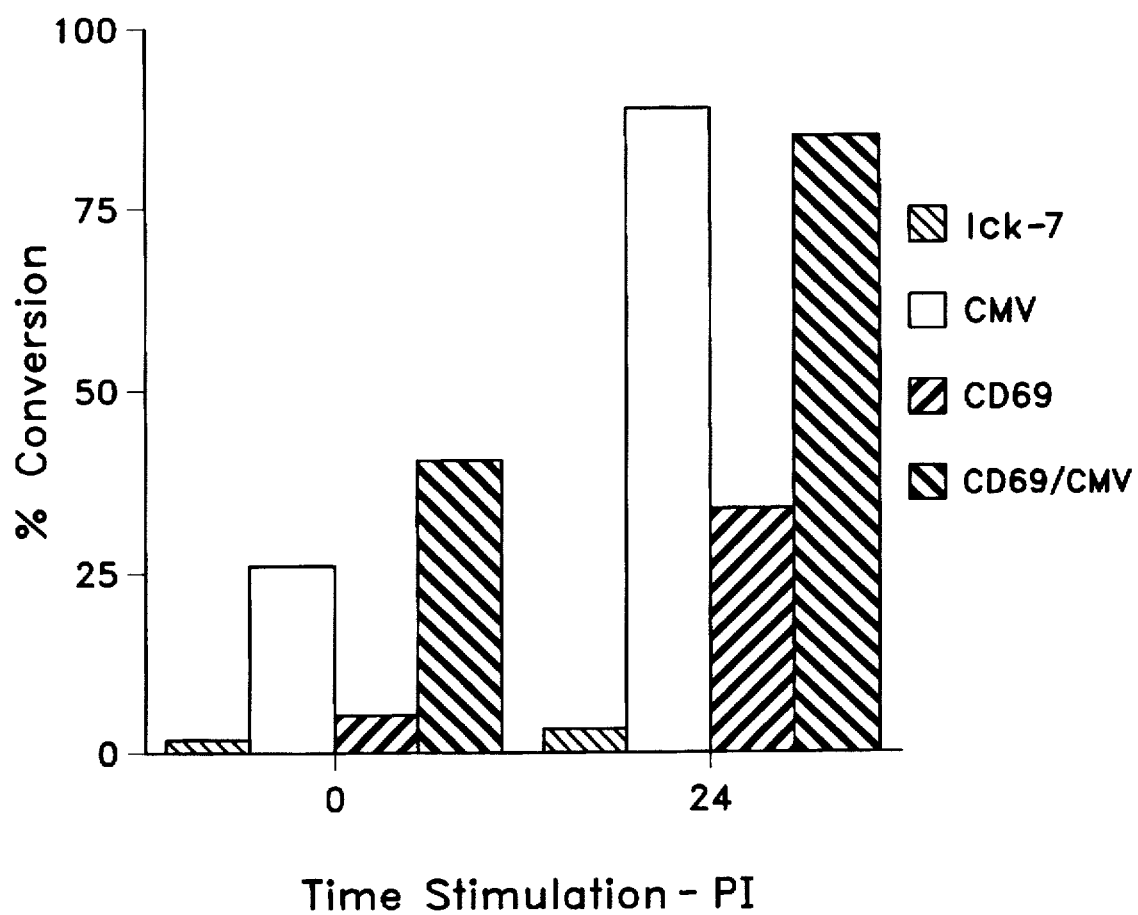
FIG. 6 is a bar graph illustrating CD69 promoter activity and its enhancement in stable transfections of Jurkat cells.
Figure 7:
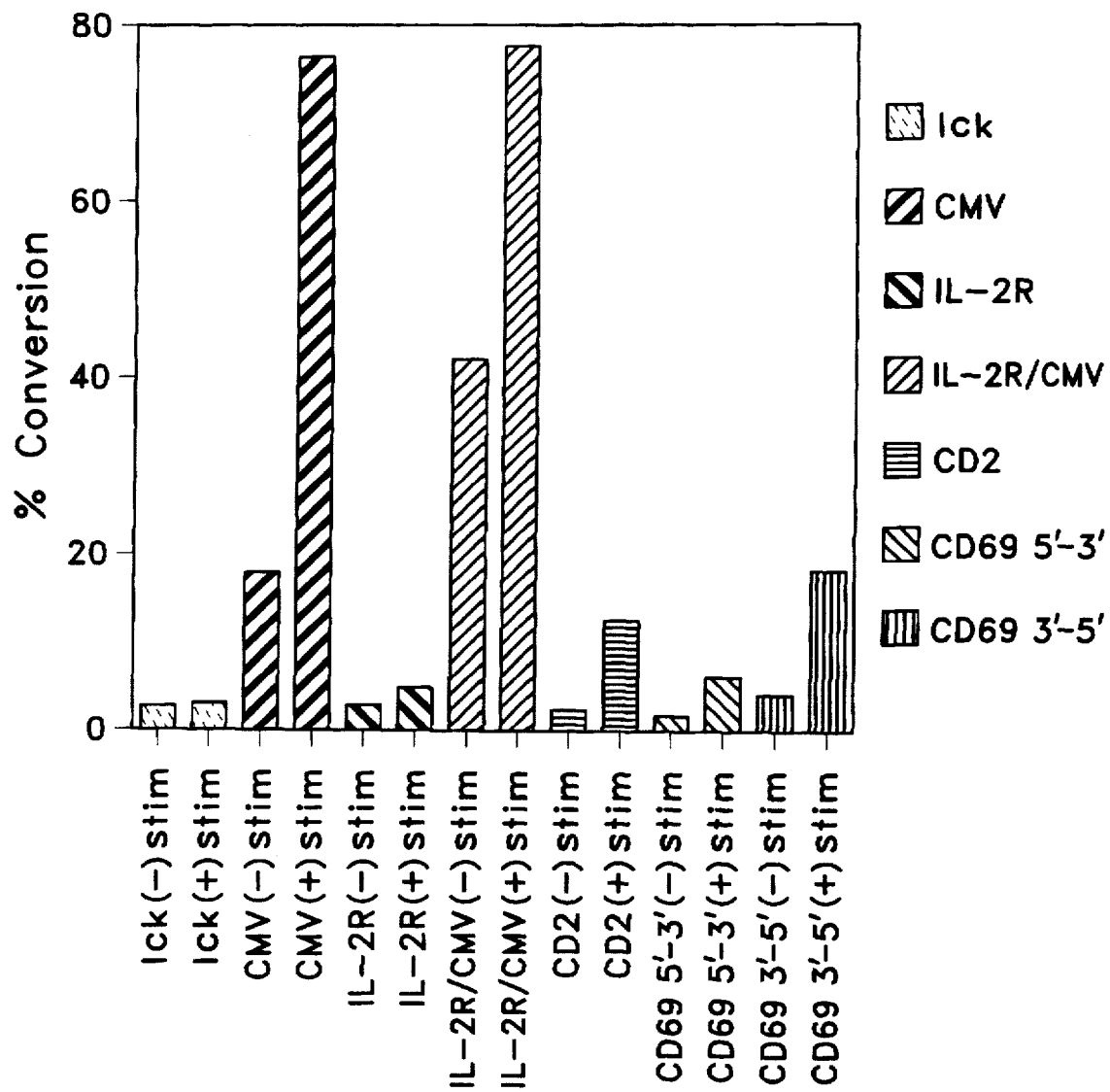
FIG. 7 is a bar graph illustrating CD69 enhancer activity using an IL-2R promoter.

The results are shown in FIG. 6. The CD69 sequences promoted CAT transcription at a low level in unstimulated cells but in contrast to transiently transfected cells, activity increased 6–10 fold in PI-stimulated cells.

Stable transfection of the HyTK-CMV-CD69HB-CAT construct into Jurkat cells resulted in high CAT activity in unstimulated cells, and was approximately 3-fold higher in stimulated cells.

Example 5

Identification of CD69 Enhancer Sequences

Additional CD69 5' sequences were present in the isolated murine genomic clones. A KpnI-HindIII fragment was isolated from clone AR5.0 (see Example 1 and inserted into the respective sites pSKCD69 HB (in which a KpnI site is present in the polylinker). This construct thus contained CD69 sequences from –1131 to +67 as shown in FIG. 1 and was named pSKCD69 KB. The CD69 sequences (KpnI-BamHI fragment) were transferred into the XhoI-BamHI site of HyTK-lck-7-CAT and named HyTK-CD69KB-CAT. This construct was stably transfected into Jurkat cells and polyclones selected as described in Example 3. CAT assays demonstrated that these CD69 sequences were capable of promoting high CAT activity in unstimulated as well as PI stimulated cells. This result was similar to that obtained with the CMV enhancer placed 5' of the CD69 HB promoter sequence suggesting that the CD69 KpnI-HindIII fragment contained the ability to function as an enhancer.

To examine the ability of the CD69 KpnI-HindIII fragment to function as an enhancer, the fragment was cloned 5' of the human IL-2Rα promoter (–395 to +16) in both orientations. These constructs were named HyTK-CD69KH5'-3'-IL-CAT and HyTK-CD69KH3'-5'-IL-CAT. Transient transfection of the above constructs demonstrated that the CD69 sequence was able to enhance CAT activity from the IL-2Rα promoter in both orientations.

The CD69 sequences containing the enhancer activity were transferred from the HyTK vector as a HindIII fragment into BLCAT2.

Figure 8:
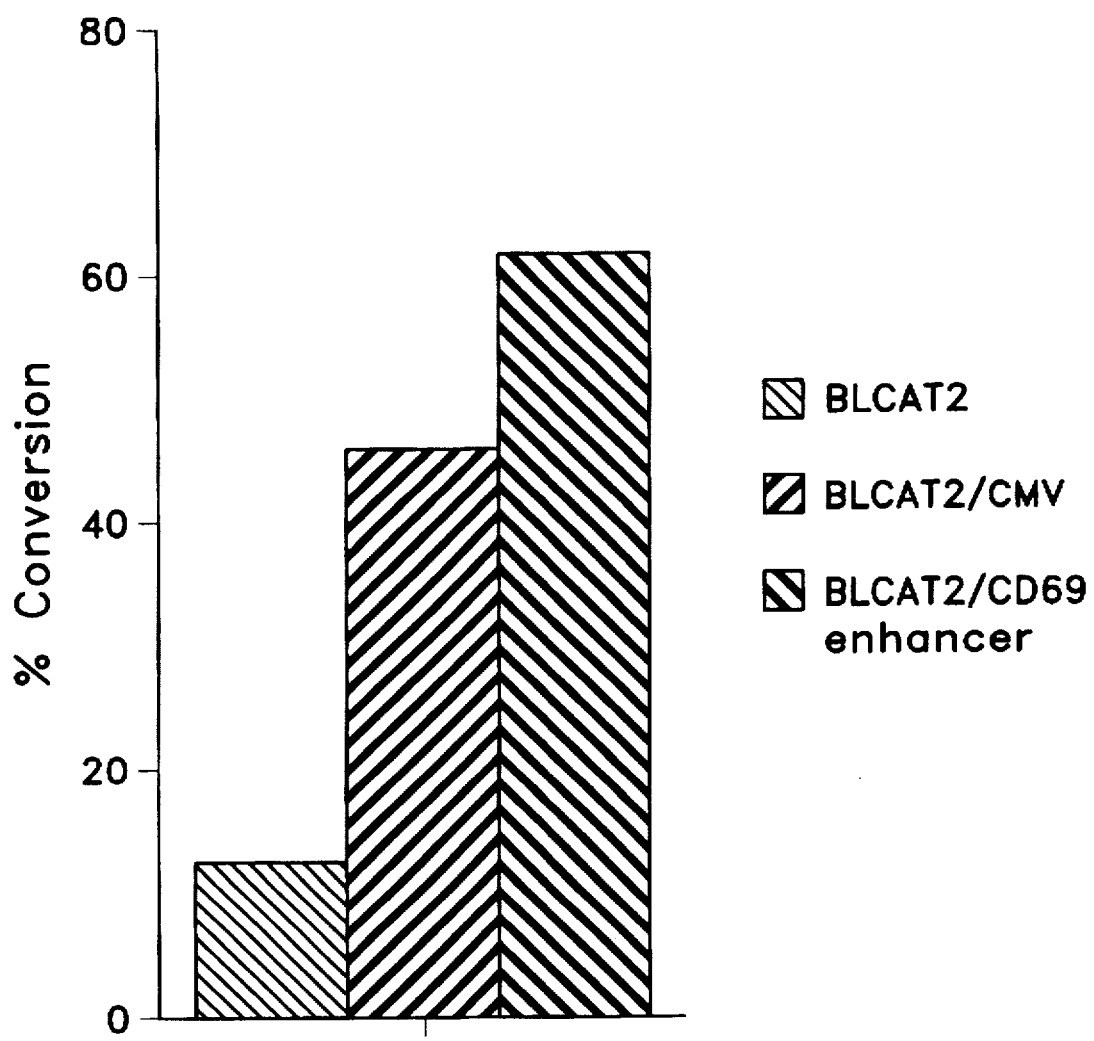
FIG. 8 is a bar graph illustrating CD69 enhancer activity compared to CMV enhancer activity using the BLCAT2 vector that includes a weak thymidine kinase promoter.

BLCAT2 contains a minimal TK promoter linked to a CAT reporter gene. The CMV enhancer was also cloned upstream of the TK promoter as a positive control. BLCAT2, BLCAT2-cmv and BLCAT2-CD69 were transiently transfected into Jurkat cells and enhancer activity measured using essentially the conditions described in Example 3. The results, shown in FIG. 8, indicate that the CD69 enhancer functioned at a level comparable to or better than the CMV enhancer.

Example 6

Isolation of the Human CD69 Gene

The human CD69 gene was isolated from a YAC clone, YAC 8105, by hybridization with 5' and 3' clones for human CD69 cDNA. A library was constructed from this YAC clone in Supercos1 cosmid vector. After a partial Sau3A digestion, the digests were cloned into the BamHI site of Supercos. The Supercos library was screened with the human CD69 cDNA probes. Clone C8105-H4 screened positive. Zeigler, et al. *Eur. J. Immunol.* (1993) 23:1643. The YAC 8105 and the human CD69 was obtained from LaRoque at the Imperial Cancer Research Foundation.

Example 7

Characterization of the CD69 Repressor

Sequences upstream of the CD69 enhancer were added to the core enhancer sequence by PCR amplification. Primers for the PCR reactions are shown on the CD69 sequence in FIG. 3. Primers 3–8 were utilized. Combinations of primers were as follows:

3+5 equivalent to KpnI-HindIII enhancer fragment

3+6 contains an additional 250 5' nucleotides over 3+5

3+7 contains an additional 360 5' nucleotides over 3+6

3+8 contains an additional 360 5' nucleotides over 3+7

4+5 contains the 3' 174 bp of the CD69 enhancer fragment

Figure 9:
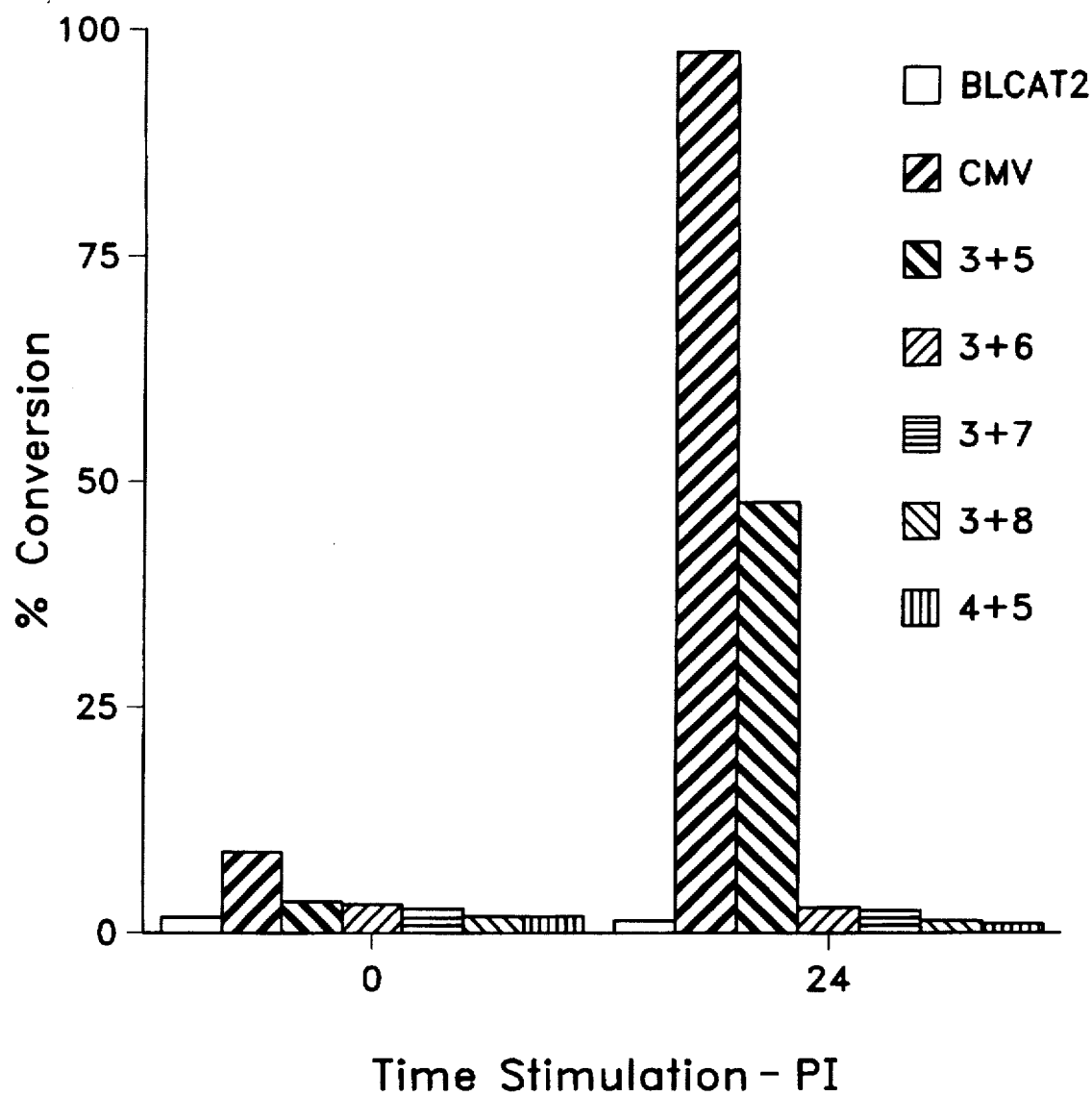
FIG. 9 is a bar graph illustrating CD69 repressor activity in a polynucleotide fragment from the upstream portion of the mouse CD69 gene.

All of the above primers contained cloning sites—HindIII at the 5' end primer and SalI at the 3' end primer. All PCR products were cloned into the HindIII-SalI sites of BLCAT2. Constructs were tested by transient transfection into Jurkat-cells, using essentially the conditions described in Example 3. Cells were unstimulated or stimulated with PI for 24 hours. The results, shown in FIG. 9, are indicative of the following promoter activity resulting from the fragments:

3+5—very active (like CMV)

3+6, 3+7, 3+8—not active—therefore, there must be a repressor between primers #5 and #6

4+5—not active—enhancer sequences must be between primers #3 and #4

---

We claim:

1. An isolated polynucleotide comprising a CD69 promoter or active fragment thereof, said promoter contained within the sequence of FIG. 3 (SEQ ID NO:1).

2. A recombinant polynucleotide comprising a CD69 promoter or active fragment thereof, said promoter contained within the sequence of FIG. 3 (SEQ ID NO:1).

3. The recombinant polynucleotide of claim 2 further comprising a coding sequence operably linked to the CD69 promoter or active fragment thereof.

4. The recombinant polynucleotide of claim 2 further comprising a coding sequence encoding a polypeptide operably linked to the CD69 promoter or active fragment thereof.

5. A recombinant expression vector comprising a coding sequence encoding a polypeptide operably linked to a CD69 promoter or active fragment thereof, said promoter contained within the sequence of FIG. 3 (SEQ ID NO:1).

6. An isolated polynucleotide comprising a CD69 enhancer, or active fragment thereof, said enhancer contained within the sequence of FIG. 3 (SEQ ID NO:1).

7. A recombinant polynucleotide comprising a promoter operably linked to a CD69 enhancer, or active fragment thereof, said enhancer contained within the sequence of FIG. 3 (SEQ ID NO:1).

8. The recombinant polynucleotide of claim 7 further comprising a coding sequence operably linked to a CD69 promoter or active fragment thereof.

9. The recombinant polynucleotide of claim 7 further comprising a coding sequence encoding a polypeptide operably linked to the promoter.

10. The recombinant polynucleotide of claim 7 wherein the promoter is a CD69 promoter.

11. A recombinant expression vector comprising a polynucleotide coding sequence encoding a polypeptide operably linked to a promoter and a CD69 enhancer, said enhancer contained within the sequence of FIG. 3 (SEQ ID NO:1).

12. An isolated polynucleotide comprising a CD69 repressor, or active fragment thereof, said repressor contained within the sequence of FIG. 3 (SEQ ID NO:1).

13. A recombinant polynucleotide comprising a promoter operably linked to a CD69 repressor or active fragment thereof, said enhancer contained within the sequence of FIG. 3 (SEQ ID NO:1).

14. The recombinant polynucleotide of claim 13 further comprising a coding sequence operably linked to the CD69 repressor or active fragment thereof.

15. The recombinant polynucleotide of claim 13 further comprising a coding sequence encoding a polypeptide operably linked to the CD69 repressor.

16. The recombinant polynucleotide of claim 13 wherein the promoter is a CD69 promoter.

17. A recombinant expression vector comprising a polynucleotide coding sequence encoding a polypeptide operably linked to a promoter and a CD69 enhancer, said repressor contained within the sequence of FIG. 3 (SEQ ID NO:1).

18. A recombinant expression vector according to claim 17 further comprising an enhancer.

19. The recombinant expression vector according to claim 18 wherein the enhancer is a CD69 enhancer.

20. A recombinant host cell comprising a polynucleotide according to any one of claims 1 to 19.

21. A method of producing a polypeptide comprising incubating a host cell transformed with a recombinant expression vector according to any one of claims 5, 11, 17, 18 and 19 under conditions that allow expression of the polypeptide.

22. A method of producing a desired RNA comprising incubating a host cell transformed with a recombinant polynucleotide comprising a CD69 promoter or active fragment thereof, said promoter contained within the sequence of FIG. 3 (SEQ ID NO:1) operably linked to a segment encoding the desired RNA, wherein the incubation is under conditions that allow transcription from the recombinant polynucleotide to produce the desired RNA.

23. A method of producing a desired RNA comprising incubating a host cell transformed with a recombinant polynucleotide comprising a CD69 enhancer or active fragment thereof, said enhancer contained within the sequence of FIG. 3 (SEQ ID NO:1), operably linked to a segment encoding the desired RNA and a promoter, wherein the incubation is under conditions that allow transcription from the recombinant polynucleotide to produce the desired RNA.

24. A method of producing a desired RNA comprising incubating a host cell transformed with a recombinant polynucleotide comprising a CD69 repressor or active fragment thereof, said repressor contained within the sequence of FIG. 3 (SEQ ID NO:1) operably linked to a segment encoding the desired RNA and a promoter, wherein the incubation is under conditions that allow transcription from the recombinant polynucleotide to produce the desired RNA.

* * * * *

UNITED STATES PATENT AND TRADEMARK OFFICE
CERTIFICATE OF CORRECTION

PATENT NO. : 5,759,805
DATED : June 2, 1998
INVENTOR(S) : Andrew L. Feldhaus et al.

It is certified that error appears in the above-identified patent and that said Letters Patent is hereby corrected as shown below:

Column 16,
Line 2, please delete "enhancer" and insert -- repressor --;

Column 17,
Line 6, please delete "enhancer" and insert -- repressor --.

Signed and Sealed this

Twenty-first Day of December, 2004

JON W. DUDAS
*Director of the United States Patent and Trademark Office*

UNITED STATES PATENT AND TRADEMARK OFFICE
CERTIFICATE OF CORRECTION

PATENT NO.   : 5,759,805
DATED        : June 2, 1998
INVENTOR(S)  : Andrew L. Feldhaus et al.

It is certified that error appears in the above-identified patent and that said Letters Patent is hereby corrected as shown below:

Column 16,
Line 56, please delete "enhancer" and insert -- repressor --;

Column 17,
Line 1, please delete "enhancer" and insert -- repressor --.

This certificate supersedes Certificate of Correction issued December 21, 2004

Signed and Sealed this

Third Day of May, 2005

JON W. DUDAS
*Director of the United States Patent and Trademark Office*

SEQUENCE LISTING ( 1 ) GENERAL INFORMATION:

( i i i ) NUMBER OF SEQUENCES: 1

( 2 ) INFORMATION FOR SEQ ID NO:1:

( i ) SEQUENCE CHARACTERISTICS:
        ( A ) LENGTH: 2149 base pairs
        ( B ) TYPE: nucleic acid
        ( C ) STRANDEDNESS: double
        ( D ) TOPOLOGY: linear ( i x ) FEATURE:
        ( A ) NAME/KEY: mat_peptide
        ( B ) LOCATION: 2080

( x i ) SEQUENCE DESCRIPTION: SEQ ID NO:1:

```
CTGACACCCG GATGGATGGA TGATTTGATG GATGGGTAGA TAGATAGATA GATAGATGGA      60

TAGATAGATA GATAGATAGA TAGATAGATA GATAGATAGA TAGATGCACG TAAATAAATA     120

AATATGGGGC TTGAGAGGTG ATGACTCAGT AGTACAGAGT TCTTATTGTT CTTTCAGAGG     180

ATCAGAGTTC AGTTCCCAGC TTAAGGAAAC TCACATTGCT TGTGACTCTA ACTCCATGGA     240

GCCTTCTTCT GTCCTCTGTG GGAACCAGCA CACACATACA TGACTCACAC ACACATAAAT     300

ATAATGCAAT TTTTTAAAAT TAAGTTTAAT AAAGGTAAAT CAATTAAAAA ATACTCACTT     360

GAGCTGCCCT TTTCCTTTAA AGAGCTTAGT TAGGACCAAC ACTTATAGCA GAGGCTGGCT     420

ATGATGACTC TCCCTGCCTA TTTTTTGTCA GTTCTGAACT CTATGAAAAC CTCATCCCAT     480

CCAACAGGCA TGAGTCAGAA GAGCACTTCT TGGTATTCAT GAGTATCTGG ACCTTCCTGC     540

TTTTCACTTG ATACTGAATT AATTACCTTA TTTATTATGG GAAAACCTGG CACATAGGCA     600

TATGGAAAAA GAACCGCTAA GACACAACCG AAAGACCTAA AGGCCCTGCA GTGGCAGGCT     660

CCTGGGCACT CCTATGGAAT AAGAAGAAGC TCTCTGTTGT AGAGGGAAAG TAATAGAGGA     720

AGTGCCCAGA GGCCAATGTA GAGGTTCTTC TTGGCTGTAA GGTCTTTGGA TTTAAGGAA     780
```

-continued

| | | | | | | |
|---|---|---|---|---|---|---|
| CCTTTATTAG | GAAGCCTTTG | GTGAGCTGAA | TGTTCTCAAC | AAGATGATAT | GACATACTTA | 840 |
| ATCTCATCCC | AGCTGCTGTG | CAGGAAAGAT | ACTGAGAACA | AAAAGTCACA | TTAGGACCAG | 900 |
| CATGTACCTG | TCTGTGTCTC | GAGCAGACAA | ATCCACCTGC | TGGCTCACCT | CATTGTCTGT | 960 |
| GCCGNNNNNG | GTACCTTCCA | AGCAACCTAA | GCATTATATC | TTCACAAAGG | GAAACCAGAC | 1020 |
| AACTTTAGTC | CAGGTCCTTT | GACAATCTCT | CCATTCTCTG | CTCTATTCCA | TATGTCAAAT | 1080 |
| GTAGAGATCA | TTCCAGAATG | TAAGAAATCA | TGCTTGTAAT | TTTTAAGAT | CCTCACACTT | 1140 |
| GACTTACCAA | AACAGACATT | TTCTGCATTT | ATGTGGTGCT | CAATAACTTA | TCTGAATGAG | 1200 |
| ATGGATATCA | TGGGAAGATA | TGTGTATAGG | GATCATCTTC | CAAATATCCG | AGGCCACAGA | 1260 |
| CACCTGAAAA | GGACATGGGG | AAATAGAAGG | AGATATTCTG | CAGTGAGACA | AAGTAAGTTT | 1320 |
| GACAGTGGAG | GATGACAAGA | AAATGAGCAA | GGGATGATGA | AATAGATAAC | TGACGAGAAA | 1380 |
| CAGGTTTTCG | ATCACACCGA | GGAAGTTTCC | AGACCACAAG | CTTTCTGTTT | CCTGCACTAA | 1440 |
| AGCAACTCCT | GACACTTGAA | AGAACTAGTC | TCTGGGGAAA | AAAGAAGTGA | ATGCCACACG | 1500 |
| TTTTAAATCC | ATAATTAACT | AAATAAAACT | TGTCCAATTG | AGAGAGAGGG | AGAGAGAGAG | 1560 |
| CCACAAAGAT | AGAGATTTTA | AAATCCCTAC | TCAACAGTAC | ATCTTCTGGC | CACCAACAGC | 1620 |
| ACCTGGTACA | TAATGGGTAT | TCAATAAATG | CCTGTACCTG | CCTACATATA | CAAAGAAACC | 1680 |
| AATGCAAAGG | ATTGCATGAA | AAAGTTTTAC | TCTCTCTTCC | AGTGCTTTTC | CATGTCAAAT | 1740 |
| ACAGCAATCT | CCAAACTTTT | AGCTCCTTGT | TTAAGATTAA | TACCCATTTC | CTAAGTTATT | 1800 |
| TTGTGTTTTT | AAAAAGTTTG | TGGAAGGATG | TCTTCGATTC | TGGGAAAATC | CCATTTATCT | 1860 |
| CTTCCTCTTG | AAGCTACAGT | TGTGAGAAAG | CACATTTCAG | ACAGCAGGGA | AAACCCGCAG | 1920 |
| CTCACCACAA | CAACACACGG | TGAAGTGTCT | AGGCCGCTGG | AGCATAAATT | AAAGAGAACT | 1980 |
| GGCTGAGTTG | AGTGAGTACA | GGGTAGGAGG | AAGGGGTGGA | GCCTAATCGA | GTATAAAGGC | 2040 |
| TGAAATCCTC | CGAGATCAAG | ACACTGAACA | AGACAGCTCC | AGCTACATCT | CTCCGTGGAC | 2100 |
| CACTTGAGAG | TCGCCAGGGA | CCTTGAGGGG | AAAAAAATTA | AAAAGGATG | | 2149 |